(12) United States Patent
Torres Farr

(10) Patent No.: US 8,900,559 B2
(45) Date of Patent: Dec. 2, 2014

(54) COMPOSITION AND PERIODICAL DELIVERY SYSTEM FOR CELLULAR REJUVENATION

(76) Inventor: Elmer Sebastian Torres Farr, Catania (IT)

( * ) Notice: Subject to any disclaimer, the term of this patent is extended or adjusted under 35 U.S.C. 154(b) by 331 days.

(21) Appl. No.: 13/014,267

(22) Filed: Jan. 26, 2011

(65) Prior Publication Data

US 2011/0142773 A1    Jun. 16, 2011

(51) Int. Cl.

| | |
|---|---|
| *A61K 8/98* | (2006.01) |
| *A61K 35/12* | (2006.01) |
| *A61K 38/45* | (2006.01) |
| *A61P 17/00* | (2006.01) |
| *A61Q 1/10* | (2006.01) |
| *A61Q 1/00* | (2006.01) |
| *A61Q 19/00* | (2006.01) |
| *G06F 17/00* | (2006.01) |
| *A61K 8/92* | (2006.01) |
| *A61K 8/49* | (2006.01) |
| *A61K 35/28* | (2006.01) |
| *A61Q 19/08* | (2006.01) |
| *A61K 38/18* | (2006.01) |
| *A61K 8/99* | (2006.01) |
| *A61Q 1/02* | (2006.01) |
| *A61K 8/66* | (2006.01) |
| *A61K 8/34* | (2006.01) |
| *A61K 8/67* | (2006.01) |
| *A61K 8/64* | (2006.01) |

(52) U.S. Cl.
CPC . *A61K 8/64* (2013.01); *A61K 8/922* (2013.01); *A61K 8/4986* (2013.01); *A61K 35/28* (2013.01); *A61Q 19/08* (2013.01); *A61K 2800/522* (2013.01); *A61K 38/1808* (2013.01); *A61K 8/99* (2013.01); *A61K 38/1866* (2013.01); *A61Q 1/02* (2013.01); *A61K 38/1833* (2013.01); *A61K 8/66* (2013.01); *A61K 8/347* (2013.01); *A61K 8/676* (2013.01); *A61Q 19/00* (2013.01)
USPC ............ 424/63; 424/93.7; 424/94.5; 700/231

(58) Field of Classification Search
CPC ..... A61K 8/347; A61K 8/4986; A61K 35/28; A61K 38/1866; A61K 38/1833; A61K 38/1808; A61K 8/64; A61K 8/66; A61K 8/676; A61K 8/922; A61K 2800/522
USPC .......................... 424/63, 93.7, 94.5; 700/231
See application file for complete search history.

(56) References Cited

U.S. PATENT DOCUMENTS

| | | | |
|---|---|---|---|
| 2003/0134781 | A1 | 7/2003 | Carmichael et al. |
| 2005/0250202 | A1* | 11/2005 | March et al. ................... 435/366 |
| 2005/0260748 | A1* | 11/2005 | Chang et al. ................... 435/366 |
| 2007/0087437 | A1 | 4/2007 | Hu |
| 2007/0224138 | A1 | 9/2007 | Gibbons |
| 2010/0055138 | A1 | 3/2010 | Margulies et al. |

FOREIGN PATENT DOCUMENTS

WO     WO 2010/013015     *   2/2010

OTHER PUBLICATIONS

Pickart (J. Biomater. Sci. Polym. Ed., 2008, 19(8), 969-988; abstract only).*
Schafer, An Innovative Approach to Dermatological Rejuvenation as a Result of Adipose Stem Cell Facial Transplantation, e-Journal of Age Management Medicine, 2010.

* cited by examiner

*Primary Examiner* — Johann R Richter
*Assistant Examiner* — Genevieve S Alley
(74) *Attorney, Agent, or Firm* — R. Ruschena Patent Agent, LLC

(57) ABSTRACT

A composition and delivery system is provided. The composition for skin treatment includes a plurality of autologous human adult adipose stem cells an activating cream, an effective amount of coenzyme Q10, an effective amount of GHK-Cu complex peptide, an effective amount of Ascorbate, an effective amount of Human Telomerase Reverse Transcriptase, an effective amount of Lipoic Acid, an effective amount of Rosa Mosqueta oil and delivery system for the composition including a housing unit, a plurality of chambers, an insulated partition defining the chambers, a plurality of internal singular vial apertures within the insulated partition connecting the chambers, an internal motor unit, a central processing unit and at least one storage container containing at least one vial.

16 Claims, 3 Drawing Sheets

COMPOSITION AND PERIODICAL DELIVERY SYSTEM FOR CELLULAR REJUVENATION

BACKGROUND

1) Field of the Invention

The present invention generally relates to the treatment of dermatological conditions by means of a topical application of a composition as well as a system of delivery for said composition, which improves and restores the health of cells from aged or damaged skin.

2) Discussion of the Related Art

There are a multitude of different intrinsic and external factors that influence skin condition and foster skin aging. These factors lead to damage and premature aging of the skin. Intrinsic factors can include genetic predisposition, the aging process, as well as specific hormone levels within an individual. External factors can include ultra-violet radiation, air pollution, smoking, and allergenic compounds. In addition to the above factors, nutrition has a strong impact on skin condition.

One of the most common external factors is ultraviolet sunlight or "photoaging." Ultraviolet rays initiate and increase lipid peroxidation in the skin. Lipid peroxidation refers to a process where free radicals cause damage to skin components such as collagen and elastin, otherwise resulting in the oxidative degradation of lipids. Lipid peroxidation can occur when photons of ultraviolet radiation generate free radicals in the skin. Inflammation, wrinkling, and roughening of the skin are some symptoms associated with skin damage from lipid peroxidation.

In fact, radical formation is a key factor in skin aging, making antioxidizing agents particularly important in reducing and preventing lipid peroxidation. Antioxidants inhibit lipid peroxidation. Natural antioxidizing enzymes such as superoxide dismutase are effective antioxidants in mitigating and preventing the damage caused by free radicals, however, natural superoxide dismutase levels decrease with aging.

Conditions and diseases can also affect the skin's integrity, health, and appearance. These include but are not limited to, acne, psoriasis, rosacea, inflammation, sunburned skin, and infection. A deficiency in essential vitamins and/or fatty acids e.g. has clear cutaneous effects. Other examples of conditions that can affect the skin's integrity, health, and appearance are infections from physical trauma to the skin such as bruising, cuts, larcerations, in-grown nails, and sores.

As the skin ages it loses elasticity. Expression and/or levels of skin proteins and other biomolecules such as collagen, elastin, extracellular matrix proteins, proteoglycans, growth factors, endogenous antioxidant enzymes, and/or Dioxyribonucleic Acid ("DNA") repair enzymes may decline substantially with age, in effect, producing undesirable changes in cosmetic appearance, including sagging, thinning, or wrinkling of the skin.

As such, periodic maintenance and treatment is the single most important factor in fighting against skin aging and deterioration. Currently, there are topical compositions formulated to improve the appearance of skin. However, many of the problems associated with prior compositions are that the elements in the compositions do not work together effectively to rejuvenate the skin.

Further, in order to effectively rejuvenate skin, periodic delivery and maintenance is essential. Currently, the ability for a consumer to implement periodic treatment is impossible given the nature of the composition and the prior art.

Accordingly, there remains a need in the art for an improved and more effective topical composition and method for periodically treating and rejuvenating aging skin. This must be one that is available and suitable for the consumer environment.

BRIEF DESCRIPTION OF THE DRAWINGS

The invention is described by way of example with reference to the accompanying drawings wherein.

DETAILED DESCRIPTION

Figure 1:
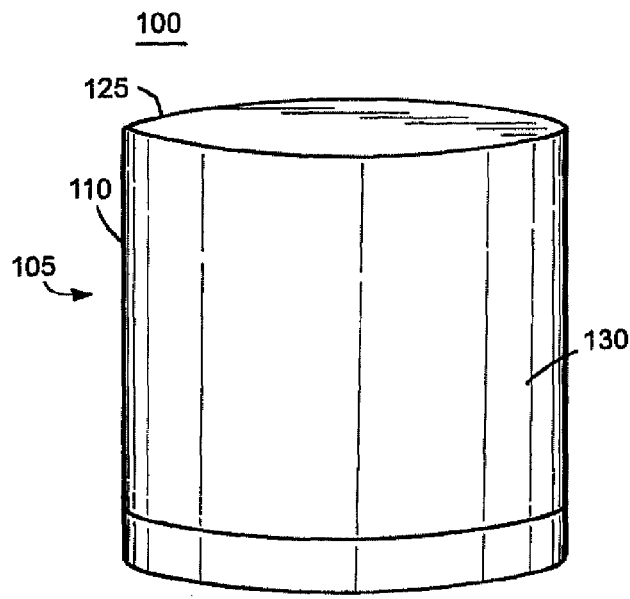
FIG. 1 illustrates a front perspective of an embodiment of a preservation delivery system.

The present invention provides anti-aging benefits to users and improves the aesthetic appearance of the skin. In particular, the present invention provides compositions and methods for treating skin to prevent, inhibit, reduce and/or ameliorate the signs of aging. Furthermore, another advantage of the invention is that it provides an "at home system" tailored for both the characteristics of the composition and ease of use for the users of the system.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

The invention relates to a composition and delivery system for improving the health of and damage to cells. A composition for skin treatment is provided. The composition includes, among other components, a plurality of autologous human adult adipose stem cells. As such, the delivery system is directed towards maintaining the integrity of the provided components such that the composition is at maximum efficacy.

An adult stem cell is thought to be an undifferentiated cell, found among differentiated cells in a tissue or organ that can renew itself and can differentiate to yield some or all of the major specialized cell types of the tissue or organ. The primary roles of adult stem cells in a living organism are to maintain and repair the tissue in which they are found. The cell it can renew and become specialized to yield specialized cell types of the tissue from which it originated.

The overall improvement in skin condition, specifically, anti-aging, has been attributed to adult adipose stem cells that are present in the transplanted fat. Human adipose stem cells can be isolated from fat tissue removed by liposuction. Adipose derived stem cells and their secretory factors can stimulate collagen synthesis and migration of fibroblasts during wound healing process.

Scientifically, collagen means any of a variety of substances that contains the alpha chains of the collagen polypeptide with a sequence that generally follows the pattern Gly-X-Y, where Gly for glycine, X for proline, and Y for proline or hydroxyproline.

Collagen is a group of naturally occurring proteins making up anywhere from 25%-35% of total protein within the body. Collagen is mostly found in fibrous tissues, cornea, cartilage, bone, blood vessels, the gut, and intervertebral disc, and is responsible for skin elasticity and its degradation, leading to wrinkles that accompany aging. Therefore, its stimulation and support are crucial in combating the aging process.

A. Composition

The components that make up the composition described herein are included to provide maximum efficacy of collagen stimulation and support. Given the foregoing, in an embodiment, the adult stems cells comprise at least 0.2 percent by weight (wt %) within the composition. In another embodiment, the effective amount of stem cell contribution includes at least 0.5 wt % in order to effectively stimulate collagen synthesis.

The composition further includes an activating cream. In an embodiment, the activating cream comprises at least one of autologous and heterologous growth factors with at least one component selected from the group consisting of epidermal growth factor, vascular endothelial growing factor, and hepatocyte growth factor.

The presence of growth factors in the composition stimulate stem cell metabolism. Growth factors can be developed in either an autologous or allogeneic fashion. Autologous growth factors are obtained from blepharoplasty or platelet rich plasma (PRP) by separating plasma from red blood cells using a low spin process. Allogenenic growth factors have generally been obtained from neonatal skin cultures.

PRP permits the body to take advantage of the normal healing pathways at an accelerated rate. Platelets are one of many cells directed towards the healing process. Platelets aid in forming blood clots and release growth factors into a wound. These platelet derived growth factors function to assist the body in repairing itself by stimulating stem cells to regenerate new tissue. The more growth factors the more stem cells are stimulated to produce new host tissue.

Growth factors are a complex family of polypeptide hormones or biological factors that are produced by the body to control growth, division and maturation of blood cells by the bone marrow. They regulate the division and proliferation of cells and influence the growth rate of some cancers.

As stated above, when free radicals and UV damage occurs, the process of stem-cell stimulation occurs naturally to replace damaged tissues, but the skin's natural repair mechanism is unable to keep up with the amount of such damage. Natural growth factors, like TGF (transforming growth factor), stimulates stem cells within or to damaged skin to multiply, migrate, and differentiate into normal, fully developed cells. This results in new tissue and a decrease in the appearance of fine lines and wrinkles.

Growth factors include cytokines and proteins and are produced by a variety of cell types. Certain growth factors are known to promote dermal fibroblast and keratinocyte (predominant cell type in the epidermis, constituting 95% of the cells found in that region) proliferation and to induce extra-cellular matrix formation including fibrillar collagen.

There are many growth factors that interact to re-establish a balanced homeostatic environment in aged and photoaged skin. In an embodiment, these will include but are not limited to: TGF-alpha, epidermal growth factor (EGF), KGF (keratinocyte growth factor), bFGF (basic fibroblast growth factor), SCF (stem cell factor), ET-I (endothelian), IGF-1 (insulin-like growth factor), CGF (connective tissue growth factor)

In an embodiment, the composition includes at least 0.3 wt % EGF. In another embodiment, the composition includes at least 0.1 wt % of Vascular Endothelial Growth Factor (VEGF). In another embodiment, the composition includes at least 0.3 wt % of Human Growth Factor (HGF). VEGF and HGF increase stem cell growth as stated above. EGF plays a role in stem cell growth, but also plays an important role in the regulation of cell proliferation and differentiation by binding to its receptor EGRF.

The composition can include the above growth factors at different percentages, as well as the following a granulocyte-macrophage colony-stimulating factor, a macrophage colony stimulating factor, a growth hormone, TSP-1, TSP-2, a collagen protein, TIMP-1, a superoxide dismutase, an elastin, or a hypoxia inducible factor, or a biologically active derivative thereof.

The composition further comprises an effective amount of coenzyme Q10. Coenzyme Q10 is a free radical inhibitor that inhibits lipid peroxides from forming in plasma membranes. Coenzyme Q10 plays a very important role in cellular energy production and works in the mitochondrial adenosine and is one of the most important lipophilic antioxidants, preventing the generation of free radicals as well as oxidative modifications of proteins, lipids, and DNA.

The structure of coenzyme Q10 is set forth below:

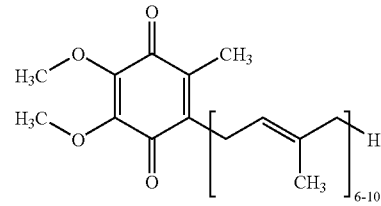

In an embodiment, the effective amount of coenzyme Q10 to enhance cellular rejuvenation within the composition is at least 0.01 wt %. At this level, stem cell metabolism and survival is enhanced and improved.

Further, the composition comprises an effective amount of GHK-Cu complex peptide. The GHK-Cu complex peptide promotes collagen and elastin synthesis, reducing the appearance of fine lines and wrinkles. This is a peptide with an amino acid sequence glycyl-L-histidyl-L-lysine, which is bound to copper. As used herein, the term "peptide copper complex" refers to a coordination compound comprising a peptide molecule and a copper ion non-covalently bound. The peptide molecule donates electrons to the copper ion to yield the non-covalent complex.

The peptide molecule is a chain of two or more amino acid units covalently bonded together via amide linkages (for example, —CONH—), the formation of such linkages being accompanied by the elimination of water. The amino acid units are from amino acids that are naturally occurring or otherwise. Also, at least one amide linkage nitrogen atom may have covalently bonded thereto either a hydrogen atom or another moiety.

Generally, an amino acid consists of an amino group, a carboxyl group, a hydrogen atom, and an amino acid side-chain moiety-all bonded, in the case of an alpha-amino acid, to a single carbon atom that is referred to as an alpha-carbon. Naturally occurring amino acids, that is, amino acids from which the amino acid units of naturally occurring proteins are derived, and their respective naturally occurring, amino acid side chain moieties, are shown below:

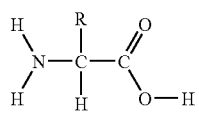

One example of a copper peptide complex is alanyl-histidyl-lysine: copper(II). Copper(II), as is well understood by the skilled artisan, designates a copper ion having a valence of 2 (e.g., Cu+2). Copper is known to have many beneficial biological applications and effecting cosmetic improvements by, or example, stimulating a variety of processes related to skin, such as collagen, elastin and glycosaminoglycan production. In an embodiment of the invention, the GHK-Cu complex peptide component comprises at least 0.5 wt % of the composition in order to enhance or improve stem cell metabolism and survival.

Further, expanding on the above, the expression "peptide copper complex," as used herein, encompasses peptide copper complex derivatives. The expression "peptide copper complex derivative," as used herein, refers to a peptide copper complex where the peptide molecule thereof has: 1) at least one amino acid side chain moiety that is a modification and/or variation of a naturally occurring, amino acid side-chain moiety; and/or 2) at least one of the hydrogens, bonded to an amide linkage nitrogen atom, substituted with a different moiety; and/or 3) the carboxyl group of the carboxyl terminal residue esterified or otherwise modified; and/or 4) at least one hydrogen, bonded to the nitrogen atom of the amino-terminal residue, substituted with a different moiety.

The composition further includes an effective amount of Ascorbate. Ascorbate generally has the structure of:

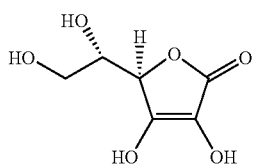

Ascorbic acid is an essential vitamin for the growth and maintenance of healthy cells in vivo and in vitro. Ascorbic acid is a water-soluble antioxidant that protects compounds from peroxidation. In fact, Vitamin C is the L-enantiomer of Ascorbic acid. Commercial Vitamin C is often a mix of Ascorbic acid, sodium ascorbate and/or other ascorbates. Ascorbic acid is an organic acid and antioxidant also known as Vitamin C.

Ascorbic acid further facilitates the mobilization of copper from serum ceiruloplasmin into cells without producing hydrogen peroxide and is a cofactor for the enzyme prolyl hydroxylase that catalyzes the post translation hydroxylation of proline residues in nascent collagen and elastin molecules. Post-translation hydroxylation of these residues increases the degree of intra-molecular cross-linking of collagen and elastin and facilitates the development of extracellular matrices.

The primary function of Ascorbic acid is to assist in the production of collagen. As such, in an embodiment, an effective amount of Ascorbate includes at least 4 wt % of the composition. In another embodiment, a form of Ascorbate includes an ester form. The invention uses Ascorbic acid because of its ability to heal wounds and burns and accelerate healing after surgery. As a participant in hydroxylation, Vitamin C is needed for the production of collagen in the connective tissue. Because skin has a greater percentage of collagen, this makes Vitamin C an important component in the invention.

However, other collagen enhancing agents such as those described herein may also be added to the present formulation. These include anthocyanidins, asiatic acid (such as from centella asiatica), aucubin, proanthocyanidins, the amino acids 1-lysine, 1-proline and their derivatives (e.g., dipalmitoyl-hydroxy-proline, hydroxyproline, homoproline, and natural raw materials containing these such as apt (*Ahnfeltia concinna*), and copper peptides.

Alternatively, in another embodiment, collagen itself may be added to the composition such as in the formation of collagen peptides (e.g. Active Collagen Polypeptide available from Shanghai UChem Co. LTD.) or in a form adapted for delivery to the skin so that the collagen will penetrate into the skin (e.g., the form described in U.S. Pat. No. 6,759,056).

Another component of the invention includes an effective amount of Human Telomerase Reverse Transcriptase (hTERT). Telomeres are the specialized repetitive DNA sequences at the ends of the linear chromosomes, and associated proteins, that serve to maintain the integrity of the chromosomes. Telomerase is a ribonucleoprotein DNA polymerase complex that maintains telomere length.

The complex comprises the protein telomerase reverse transcriptase hTERT and a catalytic RNA (TERC). The absence of telomerase activity in most human somatic cells results in telomere shortening during aging. Telomerase activity can be restored to human cells by hTERT gene transduction or potentially via drug therapy; such extended-lifespan cells could be useful in forms of cell therapy to be developed for age-related diseases. On the other hand, the absence of telomerase acts as a limitation on cancer growth unless telomerase becomes reactivated.

It has been shown that oxidants generated by mitochondria are the major source of the oxidative lesions in the mitochondria that accumulate with age. (Ames B N, et al., Biochim Biophys Acta. 1995 May 24; 1271(1):165-70). A recent study has demonstrated that over expression of hTERT, the catalytic subunit of telomerase protects fibroblasts against oxidative stress. When the cell is under oxidative stress, according to the free radical theory of aging, the mitochondrial membrane loses potential, and mtDNA is damaged as the ion levels increase. In hTERT overexpressing cells, mtDNA is protected, mitochondiral membrane potentials are higher, and concentrations of free radicals are lower which indicates better mitochondrial function and viability, which in the end means decreased damage, generally found at least 0.1 wt % of hTERT included in the composition.

The composition further includes an effective amount of Lipoic Acid. This component is structured as below:

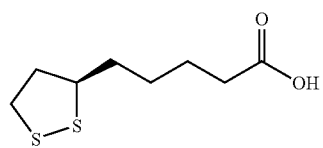 [SMILES: O=C(O)CCCC[C@@H]1CCSS1]

Lipoic Acid is an antioxidant that is water and fat soluable and is able to penetrate the skin. A "lipid" means any of a group of organic compounds, including the fats, oils, waxes, sterols, and triglycerides that are insoluble in water but soluble in nonpolar organic solvents, and are oily to the touch. Major classes of lipids include the fatty acids, the glycerol-derived lipids (including the fats and oils and the phospholipids), the sphingosine-derived lipids (including the ceramides, cerebrosides, gangliosides, and sphingomyelins), the steroids and their derivatives, the terpenes and their derivatives, certain aromatic compounds, and long-chain alcohols and waxes.

Lipoic acid provides the greatest protection against damaging free radicals when compared with other antioxidants. Alpha-lipoic acid diminishes fine lines, rejuvenates skin and boosts levels of other antioxidants within the composition. Further, R-lipoic acid is a mitochondrial antioxidant; it is implicated in mitochondrial energy production and protection from free radicals. R-lipoic acid is produced by the body and decreases in concentration during the aging process (Pick U., et al., Biochem Biophys Res Commun. 1995 Jan. 17; 206(2):724-30). Therefore, the addition of lipoic acid in an embodiment improves the overall effectiveness of the composition and counters the decrease found in aging cells.

The composition further includes an effective amount of Rosa Mosqueta oil. Rosa Mosqueta oil is an antiaging agent that enhances the overall composition. Rosa Mosqueta has been proven to stimulate skin elasticity and healing when used over stretch marks. In an embodiment, at least 1 wt % of the composition includes Rosa Mosqueta oil.

Rosa Mosqueta oil contains retinoic acid, related to retinol or vitamin A. It also contains a very rich source of essential fatty acids (EFA). Both retinol and EFA's promote skin regeneration. Studies have show that Rosa Mosqueta oil slows the signs of sun exposure-based skin aging. Both wrinkles and brown spots diminish with regular application.

The oil also improves skin elasticity, and scars from burns and surgery. Pure Rosehip oil contains around three-quarters essential fatty acids: oleic, linoleic, and linolenic, which help maintain healthy skin. Rosehip oil also contains natural Tretinoin, a derivative of Retinol (Vitamin A), which replenishes and helps rebuild skin tissue. The oil has a naturally occurring preservative in the form of anti-oxidant tocopherols (Vitamin E), helping to maintain free radicals.

More specifically, the disclosed components of the composition are useful as antioxidants, anti-aging agents, anti-wrinkle agents, anti-peroxidation agents, wound recovery agents, and integument and skin-supporting agents when applied to the skin/integument, or administered generally to an animal or human body.

The composition can be applied through a variety of means. In an embodiment, the composition can be included in make up. In another embodiment the composition can be included in foundation. In yet another embodiment, the composition can be included in a cover cream or an eye shadow, or generally any composition that can be applied to the skin. While the composition is effective on application, means to effectuate deeper penetration can include chemical peels, lasers or a dermarroller.

As such, the foregoing is considered as illustrative only and is not to be interpreted in the limiting sense. Since numerous modifications and changes will readily occur to those skilled in the art, the invention is not limited to the exact description, and accordingly, all suitable modifications and equivalents, falling within the scope of the invention are incorporated herein

EXAMPLE 1

| Ingredient | % by weight |
| --- | --- |
| Autologous adult adipose stem cells | 0.2% |
| Autologous growth factors | |
| EGF | 0.3% |
| coenzyme Q10 | 1.0% |
| GHK-Cu Complex Peptide | 0.5% |
| Ascorbate | 4.0% |
| hTERT | 0.1% |
| Lipoic Acid | 3.0% |
| Rosa Mosqueta Oil | 1.0% |

EXAMPLE 2

| Ingredient | % by weight |
| --- | --- |
| Autologous adult adipose stem cells | 0.2% |
| Autologous growth factors | |
| VEGF | 0.1% |
| coenzyme Q10 | 1.0% |
| GHK-CU Complex Peptide | 0.5% |
| Ascorbate | 4.0% |
| hTERT | 0.1% |
| Lipoic Acid | 3.0% |
| Rosa Mosqueta Oil | 1.0% |

EXAMPLE 3

| Ingredient | % by weight |
| --- | --- |
| Autologous adult adipose stem cells | 0.2% |
| Autologous growth factors | |
| HGF | 0.3% |
| coenzyme Q10 | 1.0% |
| GHK-Cu Complex Peptide | 0.5% |
| Ascorbate | 4.0% |
| hTERT | 0.1% |
| Lipoic Acid | 3.0% |
| Rosa Mosqueta Oil | 1.0% |

EXAMPLE 4

| Ingredient | % by weight |
| --- | --- |
| Autologous adult adipose stem cells | 0.2% |
| Heterologous growth factors | |
| EGF | 0.3% |
| coenzyme Q10 | 1.0% |
| GHK-CU Complex Peptide | 0.5% |
| Ascorbate | 4.0% |
| hTERT | 0.1% |
| Lipoic Acid | 3.0% |
| Rosa Mosqueta Oil | 1.0% |

EXAMPLE 5

| Ingredient | % by weight |
|---|---|
| Autologous adult adipose stem cells | 0.2% |
| Heterologous growth factors | |
| VEGF | 0.1% |
| coenzyme Q10 | 1.0% |
| GHK-Cu Complex Peptide | 0.5% |
| Ascorbate | 4.0% |
| hTERT | 0.1% |
| Lipoic Acid | 3.0% |
| Rosa Mosqueta Oil | 1.0% |

EXAMPLE 6

| Ingredient | % by weight |
|---|---|
| Autologous adult adipose stem cells | 0.2% |
| Heterologous growth factors | |
| HGF | 0.3% |
| coenzyme Q10 | 1.0% |
| GHK-CU Complex Peptide | 0.5% |
| Ascorbate | 4.0% |
| hTERT | 0.1% |
| Lipoic Acid | 3.0% |
| Rosa Mosqueta Oil | 1.0% |

2. Periodical Preservation Delivery System

Due to the nature of the components of the composition, it is necessary that certain measures be taken to prevent contamination and maintain the integrity of the composition. The device is designed to house the composition under supportive conditions in achieving maximum efficacy, and at the same time, provide "at home" users ease of use and control.

Flow cytometric analysis suggested that the biological properties of adipose-derived stem cells do not significantly change at 4 degrees Celsius up to 3 days. Thus aspirated fat can be transported to a cell-processing center for cell isolation on the day after harvesting and for subsequent banking if it is kept at 4 degrees Celsius.

Histologic examination findings of stored fat samples at −30 degrees Celsius for 1 month showed that general architecture of the tissue was maintained despite obvious reduction of the intercellular connective tissue. Transmission electron microscopy of the frozen-thawed tissue, although showing numerous cells with morphologic changes, did show preserved adipocytes.

Currently services for cryopreservation of umbilical cord stem cells are on sale all over the world. Cryopreservation includes a controlled reduction of temperature at −100 degrees Celsius, and then liquid Nitrogen ($LN_2$) exposure to obtain −196 degrees Celsius, temperature at which cells have proven to be viable for up to 30 years.

Different methods of delivering stem cells to tissues are available, all of them including a phase of cell harvesting, purification and posterior delivery. Some of those methods conclude, that for enhanced results, several treatments are needed on a regular basis, however multiple harvesting procedures are expected.

According to an embodiment, the above-mentioned composition is designed to be a periodical treatment, one without multiple harvesting. In that, a single harvesting procedure results in several applications over specified time period. It is the features and characteristics of the delivery system that support and maintain the composition during this time period, allowing for periodic application.

FIG. 1 illustrates the preservation delivery system 100 (hereinafter "Periodical Delivery System," "Delivery System," "Preservation Delivery Sysstem" and/or "PDS"). The PDS 100 includes a housing unit 105, a housing 110, an interior portion 120 (illustrated in FIG. 2), a top portion 125, an exterior portion 130, and a bottom portion 135 (illustrated in FIG. 3).

The housing unit 110 can be made of many types of materials including but not limited to metals and plastics and other materials serving to insulate and control temperature fluctuations. These materials further are of the kind that can resist or defend against corrosion. In an embodiment, a variety of coatings are used to protect against corrosion by providing a barrier to prevent or limit contact between a structure's metal surface and a corrosive environment.

Further, the shape of the housing unit 105 is generally cylindrical in design, however the housing unit 105 can comprise other shapes and designs implemented to accomplish the features as set forth below, and as such, any description herein is not designed to be limiting.

Figure 2:
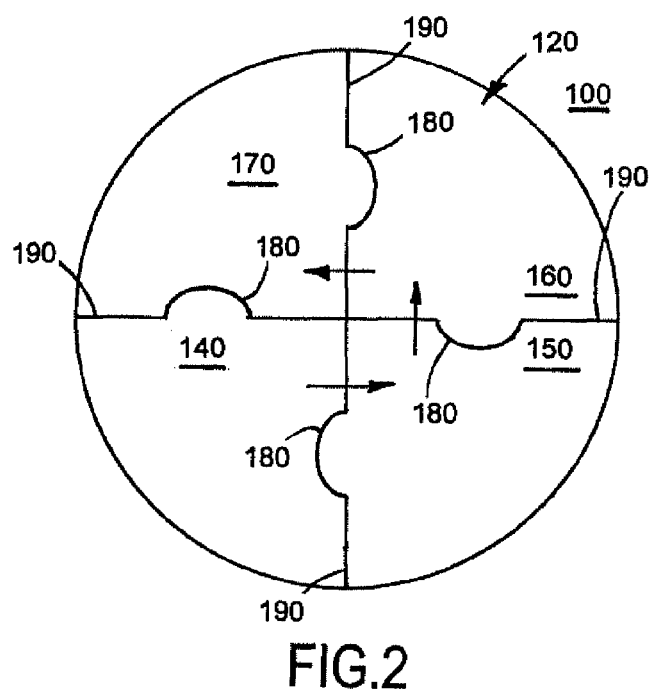
FIG. 2 illustrates a top view cross section of an embodiment of the preservation delivery system including a plurality of chambers.

FIG. 2 illustrates a top view of the PDS 100 indicating the interior portion 120. The interior portion 120 includes an initial chamber 140 characterized by a first pre-set temperature, a progressive chamber 150 characterized by a second pre-set temperature, a delivery chamber 160 characterized by a third pre-set temperature, and a discard chamber 170.

Further illustrated in FIG. 2, in an embodiment, the mentioned chambers are connected through a plurality of internal singular vial apertures 180, however, otherwise surrounded and defined by an insulated partition 190 in order to keep each chambers pre-set temperature from fluctuations. In an embodiment, the plurality of singular vial apertures 180 are connected with a mesh, plastic or rubber portion or other similar flexible barrier, allowing transmission of vials throughout the chambers, as set forth below, and at the same time, keep temperature fluctuations in respective chambers at a minimum.

The PDS 100 operates electrically and is operated by a programmable central processing unit (CPU) having the capacity to store and execute data and instructions. The CPU is electrically connected to an internal motor unit 200, illustrated in FIG. 3, and includes an automatic timer electrically connected and programmed to control the internal motor unit 200 predetermined periods. Further, the CPU includes a temperature regulator to control pre-set temperatures within the chambers.

In an embodiment, the internal motor unit 200 is connected to the housing unit 105 and rotates the housing unit 105 along an axis of rotation having a first circular path wherein the bottom portion 135 is stable. In another embodiment, the internal motor unit 200 rotates the bottom portion 135 along an axis of rotation having first circular path.

Figure 3:
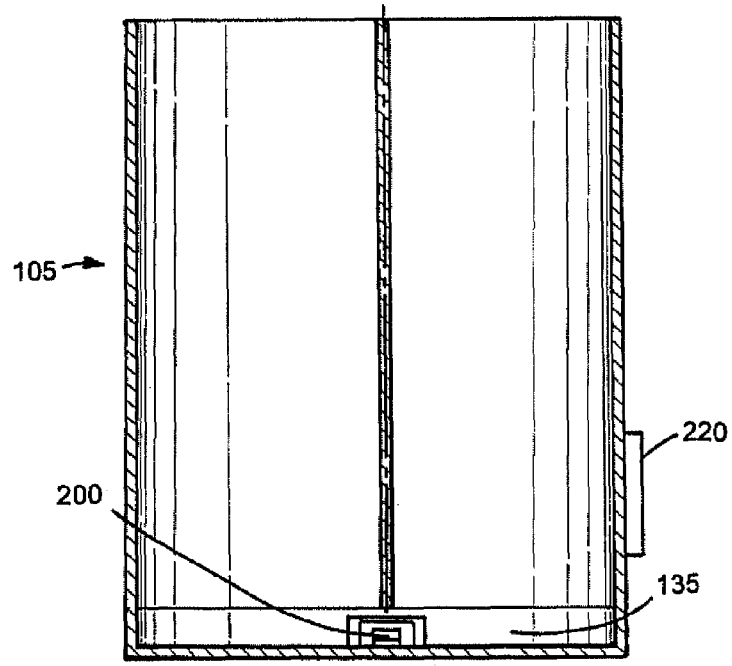
FIG. 3 illustrates a side view cross section of an embodiment of the preservation delivery system.

As further illustrated in FIG. 3, the CPU includes an automatic timer 220 programmed to control to the internal motor unit 200 for at least one predetermined period. In an embodiment, the automatic timer 220 can include a visual component located on the exterior portion 130 indicating the period of time by which the contents within the housing unit 105 can be used, as illustrated below.

As discussed above, the mentioned chambers are connected through a plurality of internal singular vial apertures 180 but surrounded by insulated partition 190 in order to keep each chamber's pre-set temperature. The preservation delivery system 100 includes a temperature regulator to aid in the pre-set temperatures of each chamber.

The temperature regulator can include a variety of cooling means including the evaporation of a liquid to absorb heat. In an embodiment, the temperature regulator can include a variety of refrigerants in maintaining or initially having a cooling effect. In an embodiment, the refrigerant can include HFCs (hydrofluorocarbons). In another embodiment, the refrigerant can include CFCs (chlorofluorocarbons) and/or HCFCs (hydrochlorofluorocarbons).

However, a variety of compounds either liquid and/or gas exist and can be used to supply the necessary temperatures and temperature ranges as mentioned herein. Along these lines, a thermometer or other temperature sensing device can be included in an embodiment, along with a regulator for adjusting a varied temperature outside that specified herein. Temperature supplying, controlling and monitoring devices are all well-known systems and present in the prior art. These systems and many other equivalents can be used herein accordingly.

As stated above, the temperature regulator maintains each of the chambers respective temperature. However, in the case of the progressive chamber 150, the chamber 150 has a second pre-set temperature indicating a range with varying temperature for its contents over a time period, in that, the chamber is progressively heated according to pre-set intervals (as described further herein). The progressive heating could be accomplished by heating water or vapor to accommodate the increase. However, a variety of other methods for increasing temperature incrementally can be used. In an embodiment, this pre-set temperature is from −30 degrees Celsius to 4 degrees Celsius, the significance of which is set forth herein.

Figure 4:
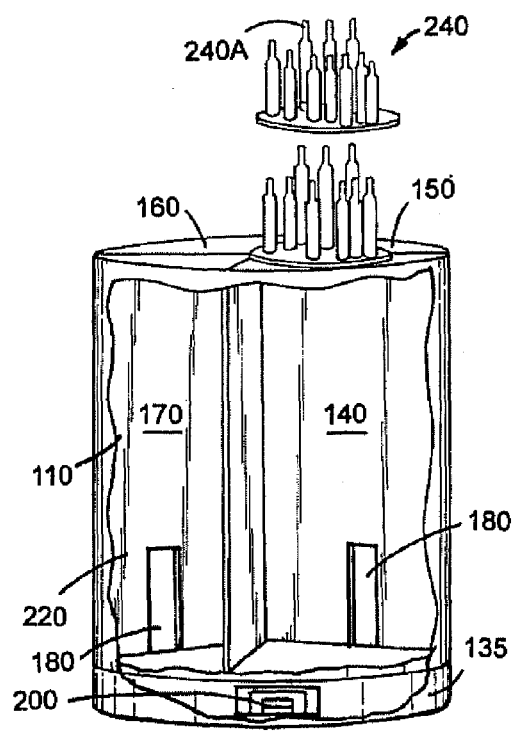
FIG. 4 illustrates an embodiment of the preservation delivery system including the loading of at least one vial.

FIG. 4 illustrates at least one storage container 240. The at least one storage container 240 is loaded into the initial chamber 140. The at least one storage container 240 holds at least one vial 240A. The at least one vial 240A (generally made of any type of glass or plastic) is transferred through the respective chambers, described below, though the singular vial aperture 180 via the operation of the internal motor unit 200 on either structure as set forth above.

FIG. 4 further illustrates another perspective of the plurality of internal singular vial apertures 180. As illustrated, the at least one vial 240A is rotated through the plurality of internal singular vial apertures 180 and exposed to varying temperatures at predefined intervals for a period as set forth below.

Figure 5:
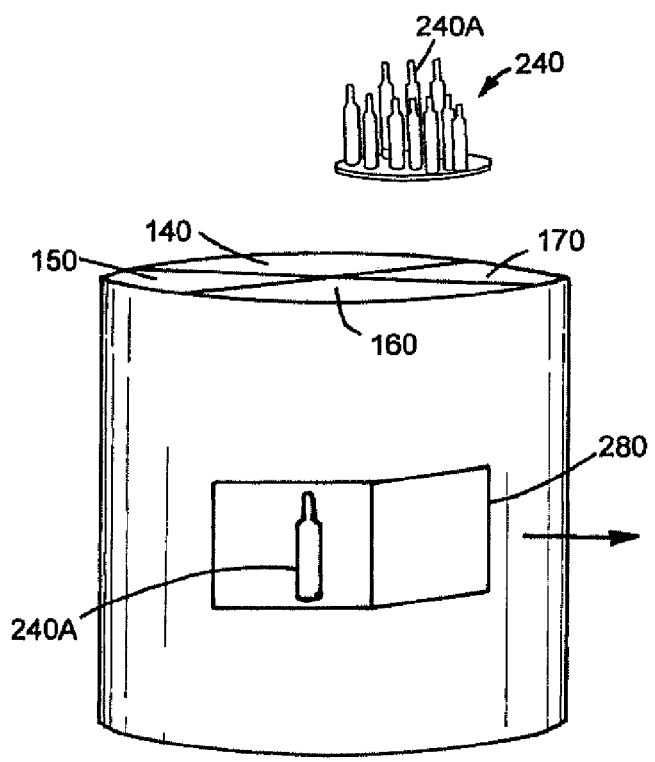
FIG. 5 illustrates a front perspective of an embodiment of the preservation delivery system including a delivery of at least one vial.

FIG. 5 illustrates an embodiment wherein the removal of the at least one vial 240A can occur through an external singular vial aperture 280 in the delivery chamber 160. In this embodiment, if within the time period specified for use of the at least one vial 240A, a user is provided the ability to retrieve the at least one vial 240A as opposed to opening up the housing unit 105 via the top portion 125. This feature is further defined below.

In use, the at least one storage container 240 with the at least one vial 240A is loaded into the initial chamber 140. In an embodiment, the initial chamber 140 stores the at least one vial at a first pre-set temperature of −30 degrees Celsius including a first predetermined time period of one (1) month. However, the range can vary from −84 degrees Celsius to −30 degrees Celsius.

The internal motor unit 200, controlled by the automatic timer of the central processing unit, rotates the housing unit 105, in an embodiment, and causes the transfer of at least one vial 240A through an internal singular vial aperture 180, into the progressive chamber 150 from the initial chamber 140. As such, in an embodiment, the at least one vial 240A would rotate into the progressive chamber 150 every 24 hours from the initial chamber 140.

In an embodiment, progressive chamber 150 second pre-set temperature serves as a progressive heating chamber wherein upon entry of the at least one vial 240A, the temperature is increased from −30 degrees Celsius to 4 degrees Celsius. In an embodiment, this increase spans a second predetermined period of 12 hours.

The internal motor unit 200, after the above second predetermined period, rotates the housing unit 105 causing the transfer of the at least one vial 240A through an internal singular vial aperture 180 into the delivery chamber 160. In an embodiment, the delivery chamber 160 includes a third pre-set temperature range of 4 Celsius-37 Celsius. In this embodiment, the third predetermined period is 24 hours. In another embodiment, the delivery chamber 160 includes a third pre-set temperature of 37 degrees Celsius for 15 minutes. In yet another embodiment, the third predetermined period is 12 hours at a temperature of 4 degrees Celsius.

Figure 6:
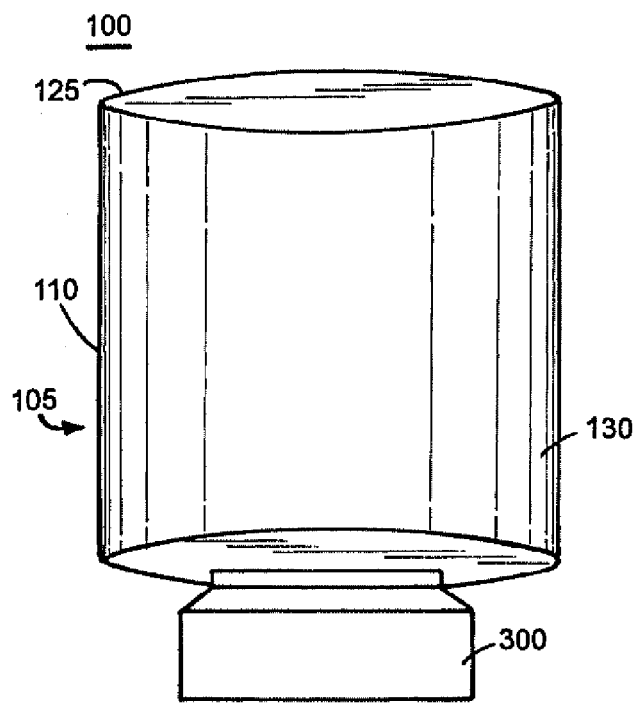
FIG. 6 illustrates a front perspective of an embodiment including a discard chamber.

It should be noted that as the third pre-set temperature range increases cellular metabolism and activity increases, however, in doing so, in an embodiment, it would result in a decrease in the third predetermined period. Otherwise, the risk of contamination and bacterial growth increases. In such an embodiment where the third predetermined period shortens, a separate compartment can be included to house discarded at least one vials 240A. This embodiment, illustrating a discard chamber 300, is illustrated in FIG. 6.

Continuing from above, if the at least one vial 240A is not used, the at least one vial 240A is caused to be transferred through an internal singular aperture 180 into the discard chamber 170 after the sum of the first, second and third predetermined periods. In an embodiment, the discard chamber 170 is connected to the discard chamber 300 (illustrated in FIG. 6) allowing space for multiple unused vials.

However, if the at least one vial 240A is used, in an embodiment, the delivery compartment 160 includes external singular vial aperture 280. This external singular vial aperture 280 is illustrated in FIG. 5, but could be located in a variety of locations along the housing unit 105, providing it allows a user ease of access to the at least one vial 240A.

As stated above, the foregoing is considered as illustrative only of the invention and is not to be interpreted in the limiting sense. Since numerous modifications and changes will readily occur to those skilled in the art, the invention is not limited to the exact description, and accordingly, all suitable modifications and equivalents, falling within the scope of the invention are incorporated herein.

The composition components are particularly advantageous because of the benefits of using adult autologous adipose derived stem cell serum with the use of adult autologous stabilized growth factors in the most effective percentages. Further, the remaining components provide a multi-pronged effect these for addressing the intersection between the skin and the internal and external factors described herein.

The addition of autologous components enhances the reparative processes in the skin for antiaging and wound management. Specifically, the use of autologous components (stem cells and growth factors) guarantees that they are immunologically compatible and active, and free of infectivity and ethical concerns.

The implementation of the preservation delivery system 100 provides many advantages over the prior art, based in large part because of initial discouraging results in adipose stem cell preservation, in that, the pre-set temperatures and predetermined periods are set to produce maximum longevity and integrity to the composition. Further, the preservation delivery system 100 allows for the home deployment and delivery of an effective skin treatment, which would otherwise be administered in a professional setting. However, currently no delivery system 100 provides for periodic delivery of a single harvest of cells. In essence, the preservation delivery system 100 constitutes a bridge between the professional setting (laboratory, medical office) and the user's home environment, while reducing trips to harvest cells for multiple applications.

As stated herein, the foregoing is considered as illustrative only of the invention and is not to be interpreted in the limiting sense. Since numerous modifications and changes will readily occur to those skilled in the art, the invention is not limited to the exact description, and accordingly, all suitable modifications and equivalents, falling within the scope of the invention are incorporated herein.

What is claimed:

1. A method of treating dermatological conditions to improve and restore the health of cells of aged or damaged epidermal area by preparing and applying a cryogenically preserved serum and an activation cream to a patient's epidermal area and wherein said method comprises:
    extracting, isolating and cryogenically preserving autologous human adipose stem cells extracted from a patient by liposuction to make an Autologous Stem Cells (ASC) serum;
    extracting from the same patient Autologous Growth Factors (AGF) using a blepharoplasty surgery, or using a Platelet Rich Plasma (PRP) extraction method;
    preparing said activation cream comprising:
        a) said extracted Autologous Growth Factors (AGF) to increase stem cell growth and to regulate cell proliferation, comprising at least one component selected from the group consisting of:
            autologous TGF-alpha Growth Factor,
            autologous Keratinocyte Growth Factor (KGF),
            autologous basic Fibroblast Growth Factor (bFGF),
            autologous Stem Cell Factor (SCF),
            autologous Insulin-like Growth Factor (IGF-1),
            autologous Connective Tissue Growth Factor (CGF),
            autologous Endothelial Growth Factor (ET-1),
            autologous Epidermal Growth Factor (EGF),
            autologous Vascular Endothelial Growth Factor (VEGF),
            autologous Hepatocyte Growth Factor (HGF),
            autologous Granulocyte-macrophage Colony Stimulating Factor,
            autologous Macrophage Colony Stimulating Factor,
            Heterologous Growth Factors (HGF) to compensate a possible lack of Autologous Growth Factors, said Heterologous Growth Factors (AGF) comprising none or any components selected from the group consisting of:
            heterologous TGF-alpha Growth Factor,
            heterologous Keratinocyte Growth Factor (KGF),
            heterologous basic Fibroblast Growth Factor (bFGF),
            heterologous Stem Cell Factor (SCF),
            heterologous Insulin-like Growth Factor (IGF-1),
            heterologous Connective Tissue Growth Factor (CGF),
            heterologous Endothelial Growth Factor (ET-1),
            heterologous Epidermal Growth Factor (EGF),
            heterologous Vascular Endothelial Growth Factor (VEGF),
            heterologous Hepatocyte Growth Factor (HGF);
            heterologous Granulocyte-macrophage Colony Stimulating Factor,
            heterologous Macrophage Colony Stimulating Factor;
        b) other activation cream components:
            an effective amount of coenzyme Q10;
            an effective amount of GHK-Cu complex peptide;
            an effective amount of Ascorbate;
            an effective amount of Human Telomerase Reverse Transcriptase (hTERT);
            an effective amount of Lipoic Acid: and
            an effective amount of Rosa Mosqueta oil;
        c) additional activation cream components:
            Growth hormone,
            Thrombospondin TSP-1,
            Thrombospondin TSP-2,
            Collagen protein,
            Glycoprotein metallopeptidase inhibitor (TIMP-1),
            Super Oxide Dismutase (SOD),
            Elastin protein,
            Hypoxia Inducible Factor or a biologically-active derivative;
    said application to a patient's epidermal area comprising:
        topical application of said Autologous Stem Cells (ASC) serum anticipated by an epidermal treatment selected from the group consisting of chemical peel, laser treatment or dermaroller; said epidermal treatment improves penetration of said serum under a patient's epidermal area;
        topical application of said activation cream to a patient's epidermal area;
    and wherein said activation cream components are included in make-up products selected from the group consisting of foundation cream, cover cream, eye shadow cream; said make-up products to be applied to the patient's epidermal area.

2. The method of claim 1 wherein said autologous adult adipose stem cells comprise 0.2% by weight.

3. The method of claim 1 wherein said autologous Epidermal Growth Factor (EGF) comprises 0.3% by weight.

4. The method of claim 1 wherein said coenzyme Q10 comprises 0.8% by weight.

5. The method of claim 1 wherein said GHK-Cu Complex Peptide comprises 0.5% by weight.

6. The method of claim 1 wherein said Ascorbate comprises 4.0% by weight.

7. The method of claim 1 wherein said Human Telomerase Reverse Transcriptase (hTERT) comprises 0.1% by weight.

8. The method of claim 1 wherein said Lipoic Acid comprises 3.0% by weight.

9. The method of claim 1 wherein said Rosa Mosqueta Oil comprises 1.0% by weight.

10. The method of claim 1 wherein said autologous growth factor VEGF comprises 0.1% by weight.

11. The method of claim 1 wherein the autologous growth factor HGF comprises 0.3% by weight.

12. The method of claim 1 wherein the heterologous growth factor EGF comprises 0.3% by weight.

13. The method of claim 1 wherein the heterologous growth factor VEGF comprises 0.1% by weight.

14. The method of claim 1 wherein the heterologous growth factor HGF comprises 0.3% by weight.

15. A method of treating dermatological conditions to improve and restore the health of cells of aged or damaged epidermal area by preparing and applying a cryogenically preserved serum and an activation cream to a patient's epidermal area and wherein said method comprises:

extracting, isolating and cryogenically preserving autologous human adipose stem cells extracted from a patient by liposuction to make an Autologous Stem Cells (ASC) serum;
preparing said activation cream comprising:
  an effective amount of coenzyme Q10;
  an effective amount of GHK-Cu complex peptide:
  an effective amount of Ascorbate;
  an effective amount of Telomerase Reverse Transcriptase (hTERT):
  an effective amount of Lipoic Acid;
  an effective amount of Rosa Mosqueta oil;
  additional components:
    Growth hormone,
    Thrombospondin TSP-1,
    Thrombospondin TSP-2,
    Collagen protein,
    Glycoprotein metallopeptidase inhibitor (TIMP-1),
    Super Oxide Dismutase (SOD),
    Elastin protein,
    Hypoxia Inducible Factor or a biologically-active derivative;
said application to a patient's epidermal area comprising:
  topical application of said Autologous Stem Cells (ASC) serum anticipated by an epidermal treatment selected from the group consisting of chemical peel, laser treatment or dermaroller; said epidermal treatment improves penetration of said serum under a patient's epidermal area;
  topical application of said activation cream to a patient's epidermal area;
and wherein said activation cream components are included in make-up products selected from the group consisting of foundation cream, cover cream, eye shadow cream; said make-up products to be applied to the patient's epidermal area.

16. A method of treating dermatological conditions to improve and restore the health of cells of aged or damaged epidermal area by preparing and applying a cryogenically preserved serum and an activation cream to a patient's epidermal area and wherein said method comprises:
  extracting from the same patient Autologous Growth Factors (AGF) using a blepharoplasty surgery, or using a Platelet Rich Plasma (PRP) extraction method;
  preparing said activation cream comprising:
  Autologous Growth Factors (AGF) to increase stem cell growth and to regulate cell proliferation, comprising at least one component selected from the group consisting of:
    autologous TGF-alpha Growth Factor,
    autologous Keratinocyte Growth Factor (KGF),
    autologous basic Fibroblast Growth Factor (bFGF),
    autologous Stem Cell Factor (SCF),
    autologous Insulin-like Growth Factor (IGF-1),
    autologous Connective Tissue Growth Factor (CGF),
    autologous Endothelial Growth Factor (ET-1),
    autologous Epidermal Growth Factor (EGF),
    autologous Vascular Endothelial Growth Factor (VEGF),
    autologous Hepatocyte Growth Factor (HGF);
    autologous Granulocyte-macrophage Colony Stimulating Factor,
    autologous Macrophage Colony Stimulating Factor,
  Heterologous Growth Factor (HGF) to compensate possible lack of autologous growth factors, said Heterologous Growth Factors (AGF) comprising none or any components selected from the group consisting of:
    heterologous TGF-alpha Growth Factor,
    heterologous Keratinocyte Growth Factor (KGF),
    heterologous basic Fibroblast Growth Factor (bFGF),
    heterologous Stem Cell Factor (SCF),
    heterologous Insulin-like Growth Factor (IGF-1),
    heterologous Connective Tissue Growth Factor (CGF),
    heterologous Endothelial Growth Factor (ET-1),
    heterologous Epidermal Growth Factor (EGF),
    heterologous Vascular Endothelial Growth Factor (VEGF),
    heterologous Hepatocyte Growth Factor (HGF);
    heterologous Granulocyte-macrophage Colony Stimulating Factor,
    heterologous Macrophage Colony Stimulating Factor,
  other activation cream components:
    an effective amount of coenzyme Q10;
    an effective amount of GHK-Cu complex peptide:
    an effective amount of Ascorbate;
    an effective amount of Human Telomerase Reverse Transcriptase (hTERT);
    an effective amount of Lipoic Acid: and
    an effective amount of Rosa Mosqueta oil;
  additional activation cream components:
    Growth hormone,
    Thrombospondin TSP-1,
    Thrombospondin TSP-2,
    Collagen protein,
    Glycoprotein metallopeptidase inhibitor (TIMP-1),
    Super Oxide Dismutase (SOD),
    Elastin protein,
    Hypoxia Inducible Factor or a biologically-active derivative;
and wherein said activation cream components are included in make-up products selected from the group consisting of foundation cream, cover cream, eye shadow cream; said make-up products to be applied to the patient's epidermal area.

* * * * *